United States Patent [19]

Englert, Jr. et al.

[11] Patent Number: 4,605,800
[45] Date of Patent: Aug. 12, 1986

[54] PROCESS FOR THE MANUFACTURE OF CHLOROPRENE

[75] Inventors: Joseph F. Englert, Jr., La Place, La.; Louis J. Maurin, III; Clare A. Stewart, Jr., both of Wilmington, Del.

[73] Assignee: E. I. Du Pont de Nemours and Company, Wilmington, Del.

[21] Appl. No.: 458,554

[22] Filed: Jan. 17, 1983

[51] Int. Cl.⁴ .............................................. C07C 17/34
[52] U.S. Cl. ..................................... 570/228; 570/229
[58] Field of Search ........................ 570/229, 228, 238

[56] References Cited

U.S. PATENT DOCUMENTS 3,664,966  5/1972  Gordon ................................ 570/228
3,981,937  9/1976  Campbell et al. .................... 570/229
4,104,316  8/1978  Scharfe et al. ....................... 570/238
4,215,078  7/1980  Hargreaves et al. ................ 570/229

Primary Examiner—Charles F. Warren
Assistant Examiner—Joseph A. Boska

[57] ABSTRACT

An improved process for the catalytic dehydrochlorination of 3,4-dichlorobutene-1 with aqueous alkali, wherein the effluent from the dehydrochlorination reactor is separated into phases, and the organic phase is steam-stripped at low temperature (below about 80° C.) to recover chloroprene product, while the steam stripper heels are returned to the dehydrochlorination reactor. A small portion of the heels are purged prior to being recycled. Most of the catalyst is recovered and returned to the reaction, but a small amount of make-up catalyst is added. Chloroprene made in this process is a valuable monomer which finds use in the manufacture of a broad line of synthetic elastomers of considerable industrial interest.

6 Claims, 2 Drawing Figures

PROCESS FOR THE MANUFACTURE OF CHLOROPRENE

BACKGROUND OF THE INVENTION

This invention relates to an improved process for the manufacture of chloroprene and particularly to an improved method of recovering it from the crude reactor effluent.

Chloroprene (2-chlorobutadiene-1,3) is an important monomer used in the manufacture of a number of synthetic elastomers. This monomer is normally made by dehydrochlorination of 3,4-dichlorobutene-1 (sometimes hereafter abbreviated to DCB) with an aqueous alkali such as sodium hydroxide. U.S. Pat. No. 3,981,937 to Campbell et al. discloses a catalytic process for carrying out this dehydrochlorination. The catalyst usually is a quaternary ammonium chloride but can also be another quaternary ammonium compound.

In one of the variants of the Campbell et al. process DCB, aqueous alkali, and the catalyst are introduced into one or more agitated reactors and are allowed to react at a moderately elevated temperature (say, 50°–70° C.) until DCB is substantially completely dehydrochlorinated. The process is normally carried out in a continuous manner since the catalyst permits high conversions at moderate temperatures and short residence times. The reactor effluent contains the chloroprene product, excess aqueous alkali, brine formed in the process, the catalyst, a minor amount of chloroprene isomer (1-chlorobutadiene), and high boiling organic materials including various polymers of chloroprene and of 1-chlorobutadiene. Chloroprene is recovered from this effluent by steam-stripping, and the remaining material is separated in a decanter into the aqueous phase and the organic phase. The latter is incinerated or otherwise disposed of; the former is pumped into deep wells following a pH adjustment and other treatment.

Valuable catalyst is lost in this recovery process because of deactivation under alkaline conditions at the steam-stripping temperature (about 90°–95° C.), which makes catalyst recovery impractical. Catalyst residues are present in the high-boiling organic phase which is incinerated. In addition to this loss, considerable energy is wasted because of the high heat input requirement in the steam-stripping step.

It thus would be highly desirable to improve the efficiency of chloroprene recovery in the catalytic process for its manufacture, reducing the catalyst loss and improving the energy utilization.

SUMMARY OF THE INVENTION

According to the present invention, there is provided in a continuous process for manufacturing chloroprene by the dehydrochlorination of 3,4-dichlorobutene-1 with aqueous alkali in the presence of a quaternary ammonium compound catalyst in one or more reactors, the improvement of separating the dehydrochlorination reactor effluent into the aqueous phase and the organic phase, steam-stripping the organic phase at a temperature of at most about 80° C. to recover crude chloroprene, discarding a small portion of the steam-stripping heels, and recirculating the remainder of the steam-stripping heels to the dehydrochlorination reaction.

DETAILED DESCRIPTION OF THE INVENTION

Figure 1:
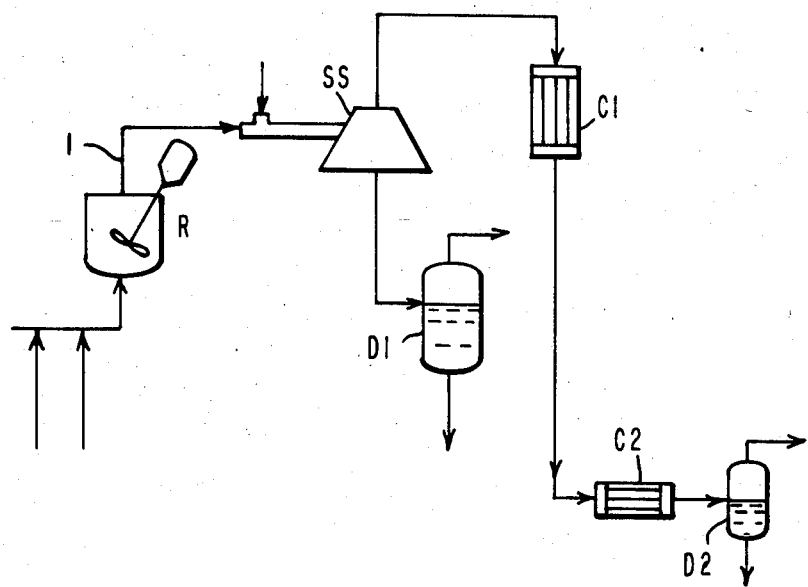
FIG. 1 is a schematic diagram of a prior art process in which chloroprene is recovered directly by steam-stripping.

Although both the prior art process and the process of the present invention are shown in the drawings as one-reactor processes, neither one is in fact so limited, and the principles of the present invention are equally applicable to a multi-reactor operation in which the reactors are arranged in a series, wherein the reactants and the catalyst may all be fed either to the same reactor or to different reactors.

Referring now to FIG. 1, R is a reactor in which DCB is dehydrochlorinated to chloroprene. In this prior art process the reactor effluent is piped through line 1 to steam-stripper SS operating at a temperature of about 90°–95° C. The volatile materials are condensed in condenser C1, cooled in heat exchanger C2, and separated in decanter D2 into the organic phase (chloroprene) and the aqueous phase. The stripper heels are separated in decanter D1 into the organic phase and the aqueous phase, and each is disposed of separately.

Figure 2:
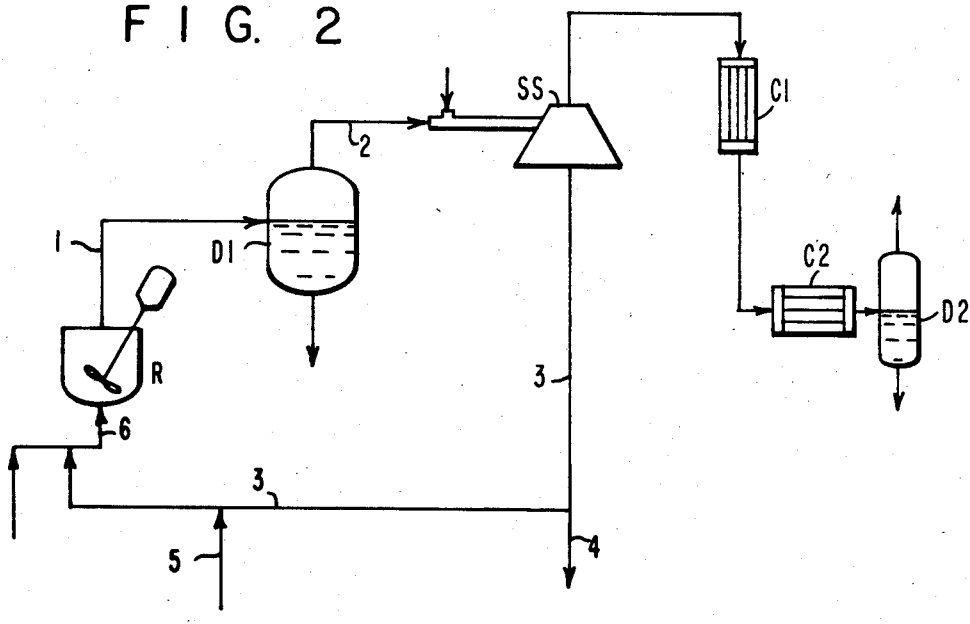
FIG. 2 is a schematic diagram of the process of the present invention.

In FIG. 2, which illustrates the instant process, R is a reactor in which DCB is dehydrochlorinated to chloroprene. The reactor effluent is introduced via line 1 into decanter D1, wherein the organic phase is separated from the aqueous phase containing brine and excess alkali. The organic phase enters through line 2 into steam-stripper SS operating at about 65°–75° C. Chloroprene is removed with the volatile materials, which are condensed in condenser C1, cooled in heat exchanger C2, and separated into phases in decanter D2. The steam-stripper heels containing, among others, water, unchanged catalyst, high boiling organic materials and some chloroprene are recycled to reactor R through line 3. A small portion of the steam-stripper heels is purged through line 4. The required amount of make-up catalyst is added to the recycle stream through line 5 and is combined with fresh DCB entering reactor R through line 6.

Although separation into phases is most conveniently carried out in a decanter (e.g., D1 and D2), other techniques may be used, for example, centrifugation, membrane separation, or electrostatic coalescence.

The usual steam-stripping temperature of the organic phase will be about 65°–75° C., which is sufficiently low to avoid substantial catalyst decomposition and deactivation. Although low temperature steam-stripping could also be carried out without prior phase separation, such an operation would be less efficient and more difficult because of the need to control foaming and would require larger equipment. When the organic and aqueous phases are separated prior to steam stripping, the steam-stripping may be carried out at a higher temperature (for example, 90°–95° C.) without substantial catalyst decomposition, provided that steam-stripper heels are promptly cooled. Such an operation is considered much less desirable, however, because of high steam and water requirements.

As an optional feature of the process of this invention, the organic phase may be treated with an acid such as, for example, acetic acid or sulfuric acid to neutralize residual alkali prior to the steam-stripping step.

The steam-stripper heels containing the bulk of unchanged catalyst are recycled to the reactor. However, because of the presence of contaminants in the steam-stripper heels, especially various polymeric materials, a portion of the heels is purged prior to being recycled to avoid excessive contaminant build-up. The amount thus removed prior to recycling will normally vary from about 2% to about 20% of the total volume of liquid.

This invention is now illustrated by the following example of DCB dehydrochlorination, wherein all parts, proportions and percentages are by weight, except as noted.

Run A was made according to the prior art process illustrated in FIG. 1, and run B was made according to the process of the present invention illustrated in FIG. 2.

In both runs eight back-mixed, liquid full reactors were arranged in a series. 3,4-Dichlorobutene-1, aqueous alkali, and catalyst or make-up catalyst were fed to the first reactor. The catalyst was cocobenzylbis($\beta$-hydroxypropyl)ammonium chloride. Aqueous alkali was a 22.6% solution of sodium hydroxide. The DCB feed rate was 11,800 parts/hr. The following additional process conditions were noted:

|  | Run A | Run B |
| --- | --- | --- |
| NaOH/DCB feed mole ratio | 1.080 | 1.089 |
| Catalyst feed rate* (parts/hr) | 39.5 | 12.2 |
| Catalyst recycled | 0 | 90% |
| Final DCB conversion | 99.59% | 99.82% |
| Steam Stripper exit temperature | 95° C. | 75° C. |
| Steam flow (parts/hr) | 4180 | 1000 |

*as 60% active catalyst solution in water

As can be seen, the fresh catalyst requirements are considerably reduced in the process of the present invention. Catalyst recycle is possible because of the lower steam stripper temperature and reduced catalyst degradation. The reduced steam-stripper temperature results in a 76% reduction of steam requirements.

I claim:

1. In a continuous process for manufacturing chloroprene by the dehydrochlorination of 3,4-dichlorobutene-1 with aqueous alkali in the presence of a quaternary ammonium compound catalyst in one or more reactors, the improvement of separating the crude dehydrochlorination product into the aqueous phase and the organic phase, steam-stripping the organic phase at a temperature of at most about 80° C. to recover the dehydrochlorination product, discarding a small portion of the steam-stripping heels, and recirculating the remainder of the steam-stripping heels to the dehydrochlorination reaction.

2. The process of claim 1 wherein the separation into phases is accomplished in a decanter.

3. The process of claim 1 wherein the portion of steam-stripping heels which is discarded is about 2% to 20% of their total volume.

4. The process of claim 3 wherein the steam-stripper exit temperature is about 65°–75° C.

5. The process of claim 1 wherein the organic phase separated from the aqueous phase following the dehydrochlorination is neutralized with an acid prior to steam-stripping.

6. The process of claim 5 wherein the acid is acetic acid or sulfuric acid.

* * * * *